(12) United States Patent
Dong et al.

(10) Patent No.: US 11,033,486 B2
(45) Date of Patent: Jun. 15, 2021

(54) PLANT COMPOSITION, PREPARATION METHOD AND APPLICATION THEREOF

(71) Applicant: NUTRI-WOODS BIO-TECH (BEIJING) CO., LTD., Beijing (CN)

(72) Inventors: Yinmao Dong, Beijing (CN); Peina Zha, Beijing (CN); Hankun Ren, Beijing (CN); Yuhong Liu, Beijing (CN); Hong Meng, Beijing (CN)

(73) Assignee: NUTRI-WOODS BIO-TECH (BEIJING) CO., LTD., Beijing (CN)

( * ) Notice: Subject to any disclaimer, the term of this patent is extended or adjusted under 35 U.S.C. 154(b) by 0 days.

(21) Appl. No.: 16/480,435

(22) PCT Filed: Jan. 12, 2018

(86) PCT No.: PCT/CN2018/072315
§ 371 (c)(1),
(2) Date: Jul. 24, 2019

(87) PCT Pub. No.: WO2018/137500
PCT Pub. Date: Aug. 2, 2018

(65) Prior Publication Data
US 2019/0380946 A1     Dec. 19, 2019

(30) Foreign Application Priority Data
Jan. 24, 2017   (CN) .......................... 201710052705.X (51) Int. Cl.
*A61K 36/00*    (2006.01)
*A61K 8/9789*   (2017.01)
*A01N 65/22*    (2009.01)
*A01N 65/28*    (2009.01)
*A61Q 19/00*    (2006.01)

(52) U.S. Cl.
CPC ............ *A61K 8/9789* (2017.08); *A01N 65/22* (2013.01); *A01N 65/28* (2013.01); *A61Q 19/00* (2013.01); *A61K 2236/331* (2013.01); *A61K 2800/5922* (2013.01)

(58) Field of Classification Search
None
See application file for complete search history.

(56) References Cited

U.S. PATENT DOCUMENTS 8,993,010 B2    3/2015   Joseph

FOREIGN PATENT DOCUMENTS

| CN | 103169639    | 6/2013 |
|----|--------------|--------|
| CN | 103655291 A *| 3/2014 |
| CN | 104398463    | 3/2015 |
| CN | 105381007    | 3/2016 |
| CN | 105475390 A *| 4/2016 |
| CN | 106266685    | 1/2017 |
| CN | 106580807    | 4/2017 |
| TW | 201023747    | 7/2010 |

OTHER PUBLICATIONS

International Search Report dated Apr. 8, 2018 in corresponding PCT Application No. PCT/CN2018/072315.
Yu, Ling et al., "Compounding of Functional Fragrances for Repelling the Mosquitoes," Flavour Fragrance Cosmetics, Dec. 31, 2006, No. 6, pp. 34-36.

* cited by examiner

*Primary Examiner* — Qiuwen Mi
(74) *Attorney, Agent, or Firm* — Duane Morris LLP (57) ABSTRACT

A plant composition, a preparation method and an application thereof. The plant composition comprises the following components in parts by weight: 20-60 parts of lemon eucalyptus, 3-20 parts of lavender, and 2-15 parts of mint. By means of adjusting the content of lemon eucalyptus, lavender and peppermint, a synergistic effect among said three components is expressed, ensuring a repellent effect while repellent time is prolonged; introducing the plant composition into skin care products enhances a repellent effect while being safe and non-irritating.

10 Claims, 3 Drawing Sheets

PLANT COMPOSITION, PREPARATION METHOD AND APPLICATION THEREOF

CROSS-REFERENCE TO RELATED APPLICATIONS

This application is a U.S. national phase application filed under 35 U.S.C. § 371 of International Application No. PCT/CN2018/072315, which was filed Jan. 12, 2018, and which claims the benefit of the filing date of CN 201710052709.X, which was filed Jan. 24, 2017. The entire content of these applications is hereby incorporated by reference herein.

TECHNICAL FIELD

The present application relates to the technical field of mosquito-repellent liquids, and more specifically relates to a plant composition, a preparation method and an application thereof.

BACKGROUND

Both zika virus and malaria are transmitted by mosquitoes. South America, Africa and Southeast Asia are areas severely afflicted by that. Accordingly, mosquito repelling is a key and difficult problem of worldwide attention. Mosquitoes often carry pathogenic bacteria such as *Staphylococcus aureus, Bacillus subtilis, Escherichia coli* and *Pseudomonas aeruginosa*, and their bite is followed by unbearable itching and even pain, which greatly affects the healthy life of people.

At present, the great majority of mosquito-repellent products available on the market contain a chemical synthetic repellent, diethyltoluamide (DEET). DEET has undoubted mosquito repellent effect but nonetheless certain safety risks such as inhibiting the activity of acetylcholinesterase, long-term exposure may induce neurological diseases. In conclusion, there is an ongoing need to develop a safe, non-irritant and truly efficacious plant mosquito-repellent raw material from a natural plant source, said plant mosquito-repellent raw material meets the market demands and has a wide application prospect and good development potential.

At present, plant mosquito repellents, which are prepared primarily by mixing or compounding a plurality of ready-made plant extracts at a certain proportion, are also available on the market. For instance, patent application No. CN 201310557700.6 discloses a preparation method of a plant mosquito repellent, which mainly comprises compounding citronella oil, mosquito-repellent grass, glycerin, mint oil, pyrethrum, lemon eucalyptus oil, lavender oil and others, however, the mosquito repellent time thereof is not explicitly mentioned, and its applications are only described as to offices, houses and living rooms. This fails to fully meet the necessary trip demand of people.

There still existing some plant mosquito repellents prepared by extracting and compounding several plant raw materials. For instance, patent application No. CN 201310495129.X discloses a plant mosquito-repellent liquid and a preparation method thereof, wherein the mosquito-repellent liquid is prepared by mixing ailanthus bark extract, aloe extract, mixed volatile oil, surfactant and ethanol. Wherein the ailanthus bark extract is prepared by extraction and concentration through a hot reflux method; the aloe extract is prepared by ultrasonic extraction and concentration; the mixed volatile oil is obtained by extraction of mosquito-repellent grass, lavender and mint leaf through steam distillation. The mosquito repellent rate thereof can reach 91% or more, and the acting time thereof can reach 5 h. However, the extraction process is relatively complex, three extraction methods are adopted therein, and concentration is indispensable, so that the cost is greatly increased in actual popularization.

The existing plant mosquito repellent is generally prepared by combining multiple plant raw materials; nevertheless, the mosquito repellent effect is not significant. Some of the plant mosquito repellents can also have other additional effects such as sterilization and itching relief while repelling mosquitoes, but they are only limited to theoretical presumption and are not supported by practical test materials. In addition, most of the existing plant mosquito repellents are not subjected to systematic toxicity evaluation, thus the safety cannot be guaranteed, and certain safety risks exist when the plant mosquito repellents are rashly applied to skin care products.

CN 105534815A provides a skin care composition containing a lotus active ingredient and a preparation method thereof, wherein the skin care composition comprises glycerin, 1,3-butanediol, squalane, polydimethylsiloxane, modified polydimethylsiloxane, dioctyl carbonate, isopropyl myristate, cetearyl alcohol, cera alba, titanium dioxide, iron oxides, sodium chloride, nuciferine, lotus pollen, allantoin, sodium hyaluronate, methylparaben, propyl 4-hydroxybenzoate, diazolidinyl urea, iron oxide red, iron oxide yellow, essence and deionized water. The skin care product can obviously improve the moisture retention of skin, but it has no mosquito repellent effect.

Hence, it appears to be particularly significant to develop a method for preparing a plant composition capable to repel mosquitoes remarkably and having a skin care effect.

SUMMARY

To solve these problems, the present application provides a plant composition, a preparation method and an application thereof. The plant composition realizes a remarkable mosquito repellent effect by the synergistic effect of the three components of lemon eucalyptus, lavender and mint, is safe and non-irritating, and can be used in skin care products.

For this purpose, the present application adopts the following technical solutions:

In a first aspect, the present application provides a plant composition, comprising the following components in parts by weight: 20-60 parts of lemon eucalyptus, 3-20 parts of lavender and 2-15 parts of mint.

The mosquito repellent effect is greatly enhanced in the present application by the mutual promotion among the lemon eucalyptus, the lavender and the mint and the synergistic effect of the three components.

In accordance with the present application, the weight parts of the lemon eucalyptus in the plant composition are 20-60 parts and may be, for example, 20 parts, 21 parts, 22 parts, 23 parts, 24 parts, 25 parts, 26 parts, 27 parts, 28 parts, 29 parts, 30 parts, 31 parts, 32 parts, 33 parts, 34 parts, 35 parts, 36 parts, 37 parts, 38 parts, 39 parts, 40 parts, 41 parts, 42 parts, 43 parts, 44 parts, 45 parts, 46 parts, 47 parts, 48 parts, 49 parts, 50 parts, 51 parts, 52 parts, 53 parts, 54 parts, 55 parts, 56 parts, 57 parts, 58 parts, 59 parts or 60 parts, preferably 30-50 parts, further preferably 33-48 parts, and specific value points between the above values. The specific value points included in said ranges are not exhaustively illustrated in the present application due to space limitation and for the sake of brevity.

In accordance with the present application, the weight parts of the lavender in the plant composition are 3-20 parts and may be, for example, 3 parts, 4 parts, 5 parts, 6 parts, 7 parts, 8 parts, 9 parts, 10 parts, 11 parts, 12 parts, 13 parts, 14 parts, 15 parts, 16 parts, 17 parts, 18 parts, 19 parts, 20 parts, preferably 5-15 parts, further preferably 5-10 parts, and specific value points between the above values. The specific value points included in said ranges are not exhaustively illustrated in the present application due to space limitation and for the sake of brevity.

In accordance with the present application, the weight parts of the mint in the plant composition are 2-15 parts and may be, for example, 2 parts, 3 parts, 4 parts, 5 parts, 6 parts, 7 parts, 8 parts, 9 parts, 10 parts, 11 parts, 12 parts, 13 parts, 14 parts, 15 parts, preferably 3-12 parts, further preferably 4-8 parts, and specific value points between the above values. The specific value points included in said ranges are not exhaustively illustrated in the present application due to space limitation and for the sake of brevity.

In a second aspect, the present application provides a preparation method of the plant composition according to the first aspect, which comprises the following steps:

(1) raw materials are pretreated;

(2) the treated raw materials are blended according to the formula amounts, then subjected to ultrasonic treatment with pure water, and extracted by distillation thereafter;

(3) the distillate obtained from the extraction in the step (2) is allowed to stand for layering, an essential oil in the upper layer is collected and blended with dipropylene glycol to obtain the plant composition.

Further, the pretreatment in the step (1) comprises pretreatment of lemon eucalyptus, pretreatment of lavender and pretreatment of mint;

The pretreatment is essential. Said pretreatment is capable of removing impurities from the raw materials so as to yield pure raw materials, and plays a role in sterilizing and killing tiny insects entrained by the raw materials. In addition, said pretreatment separates soluble components from the raw materials, and reduces certain unpleasant smells. Further, it improves extraction efficiency of the subsequent steps. Therefore, this pretreatment endows better repellent effect, higher stability and mildness to the obtained extract solution.

The pretreatment of lemon eucalyptus comprises the following specific steps: lemon eucalyptus leaves are collected and cleaned, and placed into a clean ceramic jar; then the lemon eucalyptus leaves are flipped and meanwhile sprinkled with a 30-70% ethanol aqueous solution, and thus soaked in a 30-70% ethanol aqueous solution; the lemon eucalyptus leaves are flipped once every 5-12 h and sealed for 1-3 days; then the soaked lemon eucalyptus leaves are spread uniformly, and air dried in shade until they are completely dried.

In accordance with the present application, the lemon eucalyptus are mostly planted in Fujian, Guangdong, Guangxi, Hainan, Yunnan, Sichuan, Jiangxi, Hunan and other provinces, all of which belong to the lemon eucalyptus well known in the art, and the lemon eucalyptus in the present application is derived from lemon eucalyptus cultivated in Guangxi. The lemon eucalyptus varieties from different sources do not cause the difference of the plant composition in efficacy, and do not influence the plant composition of the present application.

In accordance with the present application, in the step (1), the lemon eucalyptus is harvested, and the branches and leaves thereof can all be used for the present application, and the lemon eucalyptus leaves are preferably adopted.

Further, the concentration of the ethanol aqueous solution may be, for example, 30%, 31%, 32%, 35%, 38%, 40%, 42%, 45%, 48%, 50%, 52%, 55%, 58%, 60%, 62%, 65%, 68%, or 70%, and specific value points between the above values. The specific value points included in said ranges are not exhaustively illustrated in the present application for the sake of brevity and for the sake of clarity and simplicity.

Further, the time for flipping may be, for example, 5 h, 6 h, 7 h, 8 h, 9 h, 10 h, 11 h, or 12 h, and specific value points between the above values. The specific value points included in said ranges are not exhaustively illustrated in the present application due to space limitation and for the sake of brevity.

Further, the number of days for sealing may be, for example, 1 day, 2 days, or 3 days, and specific value points between the above values. The specific value points included in said ranges are not exhaustively illustrated in the present application due to space limitation and for the sake of brevity.

The pretreatment of lavender comprises the following specific steps: lavender flower branches are collected, cleaned, soaked in a 0.5-10% sodium chloride solution for 7-12 h, and the soaked lavender flower branches are spread uniformly, and air dried in shade;

In accordance with the present application, the lavender is planted widely, the lavender of the present application belongs to lavender well known in the art, and the lavender in the application is derived from lavender cultivated in Xinjiang. The lavender varieties from different sources do not cause the difference of the plant composition in the efficacy, and do not influence the plant composition of the present application.

In accordance with the present application, in the step (1), the lavender is harvested, and the flowers, stems and leaves thereof can all be used for the present application, and the lavender flower branches that are 25-30 cm and comprise flowers, flower stems and a small amount of leaves are preferably adopted in the present application.

Further, the concentration of the sodium chloride may be, for example, 0.5%, 0.6%, 0.7%, 0.8%, 0.9%, 1%, 2%, 3%, 4%, 5%, 6%, 7%, 8%, 9%, or 10%, and specific value points between the above values. The specific value points included in said ranges are not exhaustively illustrated in the present application due to space limitation and for the sake of brevity.

Further, the time for soaking may be, for example, 7 h, 8 h, 9 h, 10 h, 11 h, or 12 h, and specific value points between the above values. The specific value points included in said ranges are not exhaustively illustrated in the present application due to space limitation and for the sake of brevity.

The pretreatment of mint comprises the following specific steps: the mint leaves are collected, cleaned, and air dried in shade and then dried in a drying oven at 30-50° C. for 1-5 h.

In accordance with the present application, the mint belongs to mint well known in the art. The mint varieties from different sources do not cause the difference of the plant composition in efficacy, and do not influence the plant composition of the present application.

In accordance with the present application, in the step (1), the mint is harvested, and the stems and leaves thereof can all be used for the present application, and the mint leaves are preferably adopted in the present application.

Further, the drying temperature may be, for example, 30° C., 31° C., 32° C., 33° C., 35° C., 36° C., 38° C., 40° C., 41° C., 42° C., 43° C., 45° C., 48° C. or 50° C., and specific value points between the above values. The specific value points included in said ranges are not exhaustively illustrated in the present application due to space limitation and for the sake of brevity.

Further, the drying time may be, for example, 1 h, 2 h, 3 h, 4 h, or 5 h, and specific value points between the above values. The specific value points included in said ranges are not exhaustively illustrated in the present application due to space limitation and for the sake of brevity.

In the present application, the mass to volume ratio of the raw material to the pure water in the step (2) is 1:(10-50), and may be, for example, 1:10, 1:11, 1:12, 1:13, 1:15, 1:16, 1:18, 1:20, 1:21, 1:23, 1:25, 1:26, 1:28, 1:30, 1:31, 1:33, 1:35, 1:38, 1:40, 1:41, 1:43, 1:45, 1:48, or 1:50, preferably 1:(20-40), and specific value points between the above values. The specific value points included in said ranges are not exhaustively illustrated in the present application due to space limitation and for the sake of brevity.

The ultrasonic frequency in the step (2) is 28-50 kHz, and may be, for example, 28 kHz, 30 kHz, 31 kHz, 32 kHz, 35 kHz, 36 kHz, 38 kHz, 40 kHz, 41 kHz, 42 kHz, 43 kHz, 45 kHz, 48 kHz, or 50 kHz, preferably 30-45 kHz, and specific value points between the above values. The specific value points included in said ranges are not exhaustively illustrated in the present application due to space limitation and for the sake of brevity.

Preferably, the ultrasonic power in the step (2) is 100-500 W, and may be, for example, 100 W, 110 W, 120 W, 130 W, 140 W, 150 W, 160 W, 180 W, 200 W, 210 W, 230 W, 250 W, 260 W, 280 W, 300 W, 310 W, 330 W, 350 W, 380 W, 400 W, 410 W, 420 W, 430 W, 450 W, 460 W, 480 W, or 500 W, preferably 150-400 W, and specific value points between the above values. The specific value points included in said ranges are not exhaustively illustrated in the present application due to space limitation and for the sake of brevity.

Preferably, the ultrasonic temperature in the step (2) is 25-50° C., and may be, for example, 25 ° C., 26° C., 27° C., 28° C., 30° C., 31° C., 32° C., 33° C., 35° C., 36° C., 38° C., 40° C., 41° C., 43° C., 45° C., 48° C. or 50° C., preferably 30-45° C., and specific value points between the above values. The specific value points included in said ranges are not exhaustively illustrated in the present application due to space limitation and for the sake of brevity.

The ultrasonic time in the step (2) is 5-15 min, and may be, for example, 5 min, 6 min, 7 min, 8 min, 9 min, 10 min, 11 min, 12 min, 13 min, 14 min or 15 min, preferably 8-12 min, and specific value points between the above values. The specific value points included in said ranges are not exhaustively illustrated in the present application due to space limitation and for the sake of brevity.

Preferably, the duration of the distillation extraction in the step (2) is 1-5 h, and may be, for example, 1 h, 2 h, 3 h, 4 h or 5 h, preferably 1-2 h, and specific value points between the above values. The specific value points included in said ranges are not exhaustively illustrated in the present application due to space limitation and for the sake of brevity.

Preferably, the volume ratio of essential oil to dipropylene glycol in the step (3) is 1:(0.5-3), and may be, for example, 1:0.5, 1:0.6, 1:0.7, 1:0.8, 1:0.9, 1:1, 1:1.2, 1:1.5, 1:1.6, 1:1.8, 1:2, 1:2.1, 1:2.3, 1:2.5, 1:2.6, 1:2.8, or 1:3, preferably 1:(1-2), and further preferably 1:1, and specific value points between the above values. The specific value points included in said ranges are not exhaustively illustrated in the present application due to space limitation and for the sake of brevity.

In a third aspect, the present application provides a plant mosquito-repellent liquid comprising the plant composition according to the first aspect or the plant composition prepared by the preparation method according to the second aspect.

In a fourth aspect, the present application provides a skin care product comprising the plant composition according to the first aspect or the plant composition prepared by the preparation method according to the second aspect.

Further, the plant composition accounts for 5-50% by mass of the skin care product, and may account for, for example, 5%, 6%, 7%, 8%, 9%, 10%, 11%, 13%, 15%, 18%, 20%, 21%, 23%, 25%, 28%, 30%, 31%, 33%, 35%, 38%, 40%, 42%, 43%, 45%, 46%, 48% or 50%, preferably 10-40%, and specific value points between the above values. The specific value points included in said ranges are not exhaustively illustrated in the present application due to space limitation and for the sake of brevity.

In accordance with the present application, the skin care product further comprises an adjuvant.

Further, the adjuvant is an adjuvant phase A, an adjuvant phase B, an adjuvant phase C and a preservative.

Further, the adjuvant phase A is a mixture of cetearyl alcohol/cetearyl glucoside, cetearyl glucoside, polydimethylsiloxane, stearic acid, isononyl isononanoate, jojoba oil, isopropyl myristate, Ve acetate, paraffin, hydrogenated polydecene or caprylic/capric triglyceride.

Further, the adjuvant phase B is a mixture of xanthan gum, glycerol, propylene glycol, disodium ethylenediamine tetraacetic acid (EDTA), α-mannan or pyrrolidone carboxylate sodium (PCA-Na).

Further, the adjuvant phase C is acrylamide/ammonium acrylate copolymer/polyisobutylene/polysorbate-20.

The inventor unexpectedly finds that the addition of the adjuvant phase A, the adjuvant phase B and the adjuvant phase C leads to skin care effect on the basis of mosquito repelling, and the adjuvant materials and the plant extract therein are capable to work in coordination so that the mosquito repellent effect is multiplied; and the safety, the mildness and the non-irritation are verified as well through multiple (acute) skin irritation tests, acute eye irritation tests and the like.

In the present application, the adjuvant phase A comprises the following components in percentages by mass: 1.5-3% of cetearyl alcohol/cetearyl glucoside, 1-4% of polydimethylsiloxane, 0.1-3% of stearic acid, 0.1-3% of isononyl isononanoate, 0.5-6% of jojoba oil, 1-5% of isopropyl myristate, 0.5-1.5% of Ve acetate, 0.5-5% of cetearyl alcohol, 1-3% of paraffin, 3-5% of hydrogenated polydecene and 1-5% of caprylic/capric triglyceride.

Further, the percentage by mass of cetearyl alcohol/cetearyl glucoside may be, for example, 1.5%, 1.6%, 1.7%, 1.8%, 1.9%, 2%, 2.1%, 2.2%, 2.3%, 2.4%, 2.5%, 2.6%, 2.7%, 2.8% or 3%, and specific value points between the above values. The specific value points included in said ranges are not exhaustively illustrated in the present application due to space limitation and for the sake of brevity.

Further, the percentage by mass of polydimethylsiloxane may be, for example, 1%, 2%, 3% or 4%, and specific value points between the above values. The specific value points included in said ranges are not exhaustively illustrated in the present application due to space limitation and for the sake of brevity.

Further, the percentage by mass of stearic acid may be, for example, 0.1%, 0.2%, 0.3%, 0.5%, 0.6%, 0.8%, 1%, 1.2%, 1.5%, 1.8%, 2%, 2.3%, 2.5%, 2.8% or 3%, and specific value points between the above values. The specific value points included in said ranges are not exhaustively illustrated in the present application due to space limitation and for the sake of brevity.

Further, the percentage by mass of isononyl isononanoate may be, for example, 0.1%, 0.2%, 0.3%, 0.5%, 0.6%, 0.8%, 1%, 1.2%, 1.5%, 1.8%, 2%, 2.3%, 2.5%, 2.8% or 3%, and specific value points between the above values. The specific value points included in said ranges are not exhaustively illustrated in the present application due to space limitation and for the sake of brevity.

Further, the percentage by mass of jojoba oil may be, for example, 0.5%, 0.6%, 0.8%, 1%, 1.2%, 1.5%, 1.8%, 2%, 2.5%, 3%, 3.5%, 4%, 4.5%, 5%, 5.5% or 6%, and specific value points between the above values. The specific value points included in said ranges are not exhaustively illustrated in the present application due to space limitation and for the sake of brevity.

Further, the percentage by mass of isopropyl myristate may be, for example, 1%, 1.2%, 1.5%, 2%, 2.2%, 2.5%, 3%, 3.2%, 3.5%, 4%, 4.2%, 4.5% or 5%, and specific value points between the above values. The specific value points included in said ranges are not exhaustively illustrated in the present application due to space limitation and for the sake of brevity.

Further, the percentage by mass of Ve acetate may be, for example, 0.5%, 0.6%, 0.8%, 1%, 1.2%, 1.3%, 1.4% or 1.5%, and specific value points between the above values. The specific value points included in said ranges are not exhaustively illustrated in the present application due to space limitation and for the sake of brevity.

Further, the percentage by mass of cetearyl alcohol may be, for example, 0.5%, 0.6%, 0.8%, 1%, 1.2%, 1.5%, 1.8%, 2%, 2.3%, 2.5%, 2.8%, 3%, 3.2%, 3.5%, 3.8%, 4%, 4.5% or 5%, and specific value points between the above values. The specific value points included in said ranges are not exhaustively illustrated in the present application due to space limitation and for the sake of brevity.

Further, the percentage by mass of paraffin may be, for example, 1%, 1.2%, 1.5%, 1.8%, 2%, 2.5% or 3%, and specific value points between the above values. The specific value points included in said ranges are not exhaustively illustrated in the present application due to space limitation and for the sake of brevity.

Further, the percentage by mass of hydrogenated polydecene may be, for example, 3%, 3.1%, 3.2%, 3.3%, 3.5%, 3.6%, 3.8%, 4%, 4.1%, 4.2%, 4.3%, 4.5%, 4.6%, 4.8% or 5%, and specific value points between the above values. The specific value points included in said ranges are not exhaustively illustrated in the present application due to space limitation and for the sake of brevity.

Further, the percentage by mass of caprylic/capric triglyceride may be, for example, 1%, 1.2%, 1.5%, 2%, 2.2%, 2.5%, 3%, 3.2%, 3.5%, 4%, 4.2%, 4.5% or 5%, and specific value points between the above values. The specific value points included in said ranges are not exhaustively illustrated in the present application due to space limitation and for the sake of brevity.

The adjuvant phase B comprises the following components in percentages by mass: 0.05-0.2% of xanthan gum, 2-5% of glycerol, 3-5% of propylene glycol, 0.01-0.1% of disodium EDTA, 1-5% of α-mannan and 0.5-2% of PCA-Na.

Further, the percentage by mass of xanthan gum may be, for example, 0.05%, 0.06%, 0.07%, 0.08%, 0.1%, 0.12%, 0.13%, 0.15%, 0.18% or 0.2%, and specific value points between the above values. The specific value points included in said ranges are not exhaustively illustrated in the present application due to space limitation and for the sake of brevity.

Further, the percentage by mass of glycerol may be, for example, 2%, 2.2%, 2.5%, 3%, 3.2%, 3.5%, 4%, 4.2%, 4.5% or 5%, and specific value points between the above values. The specific value points included in said ranges are not exhaustively illustrated in the present application due to space limitation and for the sake of brevity.

Further, the percentage by mass of propylene glycol may be, for example, 3%, 3.1%, 3.2%, 3.3%, 3.4%, 3.5%, 3.8%, 4%, 4.2%, 4.5%, 4.8% or 5%, and specific value points between the above values. The specific value points included in said ranges are not exhaustively illustrated in the present application due to space limitation and for the sake of brevity.

Further, the percentage by mass of disodium EDTA may be, for example, 0.01%, 0.02%, 0.03%, 0.04%, 0.05%, 0.06%, 0.07%, 0.08%, 0.09% or 0.1%, and specific value points between the above values. The specific value points included in said ranges are not exhaustively illustrated in the present application due to space limitation and for the sake of brevity.

Further, the percentage by mass of α-mannan may be, for example, 1%, 1.2%, 1.5%, 2%, 2.2%, 2.5%, 3%, 3.2%, 3.5%, 4%, 4.2%, 4.5%, or 5%, and specific value points between the above values. The specific value points included in said ranges are not exhaustively illustrated in the present application due to space limitation and for the sake of brevity.

Further, the percentage by mass of PCA-Na may be, for example, 0.5%, 0.6%, 0.7%, 0.8%, 0.9%, 1%, 1.2%, 1.5%, 1.6%, 1.8%, or 2%, and specific value points between the above values. The specific value points included in said ranges are not exhaustively illustrated in the present application due to space limitation and for the sake of brevity.

Further, the adjuvant phase C accounts for 0.2-1% by mass of the skin care product, and may account for, for example, 0.2%, 0.3%, 0.4%, 0.5%, 0.6%, 0.7%, 0.8%, 0.9% or 1%, and specific value points between the above values. The specific value points included in said ranges are not exhaustively illustrated in the present application due to space limitation and for the sake of brevity.

The adjuvant phase C of the present application may be acrylamide/ammonium acrylate copolymer/polyisobutylene/polysorbate-20.

Further, the preservative accounts for 0.05-0.2% by mass of the skin care product, and may account for, for example, 0.05%, 0.06%, 0.07%, 0.08%, 0.1%, 0.11%, 0.12%, 0.13%, 0.14%, 0.15%, 0.16%, 0.17%, 0.18% or 0.2%, and specific value points between the above values. The specific value points included in said ranges are not exhaustively illustrated in the present application due to space limitation and for the sake of brevity.

As a preferred technical solution, the skin care product comprises the following components in percentages by mass:

the adjuvant phase A: 1.5-3% of cetearyl alcohol/cetearyl glucoside, 1-4% of polydimethylsiloxane, 0.1-3% of stearic acid, 0.1-3% of isononyl isononanoate, 0.5-6% of jojoba oil, 1-5% of isopropyl myristate, 0.5-1.5% of Ve acetate, 0.5-5% of cetearyl alcohol, 1-3% of paraffin, 3-5% of hydrogenated polydecene and 1-5% of caprylic/capric triglyceride;

the adjuvant phase B: 0.05-0.2% of xanthan gum, 2-5% of glycerol, 3-5% of propylene glycol, 0.01-0.1% of disodium EDTA, 1-5% of α-mannan and 0.5-2% of PCA-Na;

the adjuvant phase C: 0.2-1% of acrylamide/ammonium acrylate copolymer/polyisobutylene/polysorbate-20;

the plant composition according to claim 1 or 2: 10-40%;

preservative: 0.05-0.2%;

with the balance being water.

In a fifth aspect, the present application provides a preparation method of the skin care product according to the fourth aspect, comprising the following steps:

(1) butanediol, glycerol and xanthan gum of the adjuvant phase B are stirred uniformly for later use; the remaining raw materials of the adjuvant phase B are added into water, uniformly stirred, and the obtained mixture is added into the mixture of butanediol, glycerol and xanthan gum, then the resulting mixture is heated to 80-85° C. and mixed uniformly;

(2) the materials of adjuvant phase A is heated to 80-85° C., and mixed uniformly;

(3) all the adjuvant phase A of the step (2) are added to adjuvant phase B of the step (1), homogenized at 2000-3000 r/min for 5-10 min, then the adjuvant phase C is added thereto, homogenized at 2000-3000 r/min for 1-3 min, and then stirred at a rotation rate of 30-50 r/min for 5-10 min, thereafter, the temperature is lowered at a cooling rate of 1-2° C./min by stirring at a stirring rate of 30-50 r/min;

(4) when the temperature is lowered to 45-50° C., the plant composition according to claim 1 or 2 and the preservative are added, stirred uniformly, and the temperature is continued to be lowered to 40° C. or less, then the skin care product is obtained.

As compared to the existing technologies, the present application has at least the following beneficial effects:

(1) the plant composition of the present application has a remarkable mosquito repellent effect, the repellent time reaches the national standard for repellents (GB/T13917.9-2009), and the repellent time for actual normal use of people can reach 8 h or more, meeting people's necessary travel needs;

(2) the plant composition of the present application is capable to effectively inhibit germs generally carried by mosquitoes, and has particularly evident effect of inhibiting *Bacillus subtilis;*

(3) the plant composition of the present application can serve as a raw material of a skin care product, has no irritation to skin and eyes and is extremely mild, possesses dual effects of repelling mosquitoes and protecting skin, and can prolong the repellent time as well;

(4) the preparation method of the plant composition of the present application is simple, low in cost, and conducive to industrialized production, which lays a foundation for marketization.

DETAILED DESCRIPTION

Examples are set forth below in order to facilitate an understanding of the present application. It should be appreciated by those skilled in the art that the examples are only intended to aid in understanding the present application but not to be regarded as a specific limitation thereto.

Example 1

(1) raw materials were pretreated:

Lemon eucalyptus: Lemon eucalyptus cultivated in Guangxi was selected, wherein the selected part was lemon eucalyptus leaf. Lemon eucalyptus leaves were collected, cleaned with clear water, and placed into a clean ceramic jar, wherein the lemon eucalyptus leaves were flipped and meanwhile sprinkled with 30% ethanol aqueous solution. After the lemon eucalyptus leaves were sprinkled evenly, the jar mouth was sealed. The lemon eucalyptus leaves were soaked in 30% ethanol aqueous solution for 3 days and flipped every 12 h. Then the soaked lemon eucalyptus leaves were spread uniformly, and air dried in shade until they were completely dried.

Lavender: lavender artificially cultivated in Xinjiang was selected, wherein the selected part was flower branches with a length of about 30 cm comprising flowers, flower stems and a small amount of leaves. Lavender flower branches were collected, cleaned with clear water, and added to 0.5% sodium chloride solution and soaked for 12 h. Then the soaked lavender flower branches were spread uniformly, and air dried in shade for later use.

Mint: the selected part is mint leaf. Mint leaves were collected, cleaned with clear water, air dried in shade, then transferred to a drying oven and dried at 30° C. for 5 h for later use.

(2) the above plant raw materials were crushed and weighed according to the proportion of the following weight parts: 30 parts of lemon eucalyptus, 20 parts of lavender and 15 parts of mint, and blended uniformly;

(3) ultrasonic was conducted at 25° C., 50 kHz and 100 W for 15 min with a ratio of raw material to pure water being 1:50 g/mL, then the mixture was transferred to a distillation device and kept slightly boiled, distilled for 1 h for extraction, and the distillate was collected;

(4) the distillate obtained in the step (3) was allowed to stand for a period of time until it was naturally layered;

(5) the distilled water in the lower layer was filtered out, and the essential oil in the upper layer was collected;

(6) the collected essential oil was mixed with dipropylene glycol at a ratio of 1:3 and then the plant composition was obtained.

Example 2

(1) raw materials were pretreated:

Lemon eucalyptus: Lemon eucalyptus cultivated in Guangxi was selected, wherein the selected part was lemon eucalyptus leaf. Lemon eucalyptus leaves were collected, cleaned with clear water, and placed into a clean ceramic jar, wherein the lemon eucalyptus leaves were flipped and meanwhile sprinkled with 70% ethanol aqueous solution. After the lemon eucalyptus leaves were sprinkled evenly, the jar mouth was sealed. The lemon eucalyptus leaves were soaked in 70% ethanol aqueous solution for 1 day and flipped every 5 h. Then the soaked lemon eucalyptus leaves were spread uniformly, and air dried in shade until they were completely dried.

Lavender: lavender artificially cultivated in Xinjiang was selected, wherein the selected part was flower branches with a length of about 30 cm comprising flowers, flower stems and a small amount of leaves. Lavender flower branches were collected, cleaned with clear water, and added to 10% sodium chloride solution and soaked for 7 h. Then the soaked lavender flower branches were spread uniformly, and air dried in shade for later use.

Mint: the selected part was mint leaf. Mint leaves were collected, cleaned with clear water, air dried in shade, then transferred to a drying oven and dried at 50° C. for 1 h for later use.

(2) the above plant raw materials were crushed and weighed according to the proportion of the following weight parts: 60 parts of lemon eucalyptus, 5 parts of lavender and 5 parts of mint, and blended uniformly;

(3) ultrasonic was conducted at 45° C., 28 kHz and 500 W for 10 min with a ratio of raw material to pure water being 1:20 g/mL, then the mixture was transferred to a distillation device and kept slightly boiled, distilled for 5 h for extraction, and the distillate was collected;

(4) the distillate obtained in the step (3) was allowed to stand for a period of time until it was naturally layered;

(5) the distilled water in the lower layer was filtered out, and the essential oil in the upper layer was collected;

(6) the collected essential oil was mixed with dipropylene glycol at a ratio of 1:0.5 and then the plant composition was obtained.

Example 3

(1) raw materials were pretreated:

Lemon eucalyptus: Lemon eucalyptus cultivated in Guangxi was selected, wherein the selected part was lemon eucalyptus leaf. Lemon eucalyptus leaves were collected, cleaned with clear water, and placed into a clean ceramic jar, wherein the lemon eucalyptus leaves were flipped and meanwhile sprinkled with 50% ethanol aqueous solution. After the lemon eucalyptus leaves were sprinkled evenly, the jar mouth was sealed. The lemon eucalyptus leaves were soaked in 50% ethanol aqueous solution for 2 days and flipped every 8 h. Then the soaked lemon eucalyptus leaves were spread uniformly, and air dried in shade until they were completely dried.

Lavender: lavender artificially cultivated in Sinkiang was selected, wherein the selected part was flower branches with a length of about 30 cm comprising flowers, flower stems and a small amount of leaves. Lavender flower branches were collected, cleaned with clear water, and added to 5% sodium chloride solution and soaked for 10 h. Then the soaked lavender flower branches were spread uniformly, and air dried in shade for later use.

Mint: the selected part was mint leaf. Mint leaves were collected, cleaned with clear water, air dried in shade, then transferred to a drying oven and dried at 40° C. for 3 h for later use.

(2) the above plant raw materials were crushed and weighted according to the proportion of the following weight parts: 33 parts of lemon eucalyptus, 15 parts of lavender and 12 parts of mint, and blended uniformly;

(3) ultrasonic was conducted at 50° C., 40 kHz and 200 W for 5 min with a ratio of raw material to pure water being 1:10 g/mL, then the mixture was transferred to a distillation device and kept slightly boiled, distilled for 1.5 h for extraction, and the distillate was collected;

(4) the distillate obtained in the step (3) was allowed to stand for a period of time until it was naturally layered;

(5) the distilled water in the lower layer was filtered out, and the essential oil in the upper layer was collected;

(6) the collected essential oil was mixed with dipropylene glycol at a ratio of 1:1 and then the plant composition was obtained.

Example 4

This example was the same as Example 3 except for 40 parts of lemon eucalyptus, 15 parts of lavender and 10 parts of mint.

Example 5

This example was the same as Example 3 except for 45 parts of lemon eucalyptus, 10 parts of lavender and 10 parts of mint.

Comparison Example 1

This example was the same as Example 5 except for no lemon eucalyptus, 35 parts of lavender and 30 parts of mint.

Comparison Example 2

This example was the same as Example 5 except for no lavender, 45 parts of lemon eucalyptus and 20 parts of mint.

Comparison Example 3

This example was the same as Example 5 except for no mint, 45 parts of lemon eucalyptus and 20 parts of lavender.

Comparison Example 4

This example was the same as Example 5 except for 10 parts of lemon eucalyptus, 8 parts of lavender and 3 parts of mint.

Comparison Example 5

This example was the same as Example 5 except for 20 parts of lemon eucalyptus, 20 parts of lavender and 25 parts of mint.

The relevant tests were performed on Examples 1-5 and Comparative Examples 1-5, and said tests are as follows:

1) Mosquito Repellent Function

Products of Examples 1-5 and Comparison Examples 1-5 and the existing mosquito repellent products were subjected to a mosquito repellent effect test, and the repellent effect was determined by a method according to the national standard GBT 13917.9-2009 "Laboratory efficacy test methods and criterions of public health insecticides for pesticide registration—Part 9: Repellent". The aforesaid samples were applied in an equal amount of 1.5 mg/cm$^2$.

The specific test method is as follows:

Mosquitoes tested: sensitive Aedes albopictus, which were adult female mosquitos that were 3-5 days post-emergence and had not received a blood meal.

Test environment: temperature (26±1)° C., relative humidity (65±10)%.

Mosquito cage for test: a length of 400 mm×a width of 300 mm×a height of 300 mm.

Test Method:

① Aggressivity Assay:

300 test insects were introduced into the mosquito cage, and the back of a hand of a subject was adapted to have 40 mm×40 mm of skin being exposed while the rest was tightly shielded. The hand was put into the mosquito cage for a residence time of 2 min, and close observation was performed. Once a mosquito was observed to land on the back of the hand, the arm was shaken to drive the mosquito away in prior to its mouth part pierced the skin, and such an occurrence was recorded as that one test insect landed. The subject that attracted more than 30 test insects to land on the back of the hand and the test insects therein were qualified in aggressivity, and such a subject and such a cage of mosquitoes could be used for repellency assay.

② Repellency Assay:

6-8 subjects qualified in aggressivity (half male and half female, and no wine, tea or coffee was drunk and no essence-containing product was used by them prior to and during the test) were selected for the test. Skin areas of 50 mm×50 mm were marked out on each of the backs of both hands of these subjects, and the sample to be tested was uniformly applied on one hand at a dose of 1.5 µL/cm$^2$ or 1.5 mg/cm$^2$, with 40 mm×40 mm of skin therein being exposed and the rest being tightly shielded, and the other hand was served as a blank control. After 1 h application of the sample to be tested, the hands were put into a mosquito cage qualified in aggressivity for 2 min to determine whether there were mosquitoes landing thereon to suck blood by observation. Thereafter, the assay was performed once every 1 h, and the repellent would be judged as losing efficacy as long as one mosquito in the test group was observed to land thereon to suck blood. The effective protection time (h) of the repellents was recorded. Each time, the control hand was firstly subjected to a control test, the test insects qualified in aggressivity could be used for further test, and the test insects unqualified in aggressivity needed to be replaced with qualified ones for further test.

Test Result Statistics:

The effective protection time of the tested sample for the 6-8 subjects was summed and the average thereof (retaining 2 decimal places) was taken as the effective protection time (h) of the sample.

The results are shown in Table 1 below:

TABLE 1

|  | Time (h) |
| --- | --- |
| Example 1 | 3.8 |
| Example 2 | 3.9 |
| Example 3 | 4 |
| Example 4 | 4.2 |
| Example 5 | 4.5 |
| Comparison Example 1 | 1.9 |
| Comparison Example 2 | 2.7 |
| Comparison Example 3 | 2.3 |
| Comparison Example 4 | 1.7 |
| Comparison Example 5 | 2.0 |
| Commercially available product | 0.5 |

As can be seen from Table 1, compared with Comparison Examples 1-5, the repellent time was greatly improved in Examples 1-5 by adjusting the ratio of lemon eucalyptus, lavender and mint; in addition, compared with Examples 1-3, the repellent time was further improved in Examples 4-5 by further controlling the mass parts of lemon eucalyptus, lavender and mint within 30-50 parts, 5-15 parts and 3-12 parts respectively.

Figure 1:
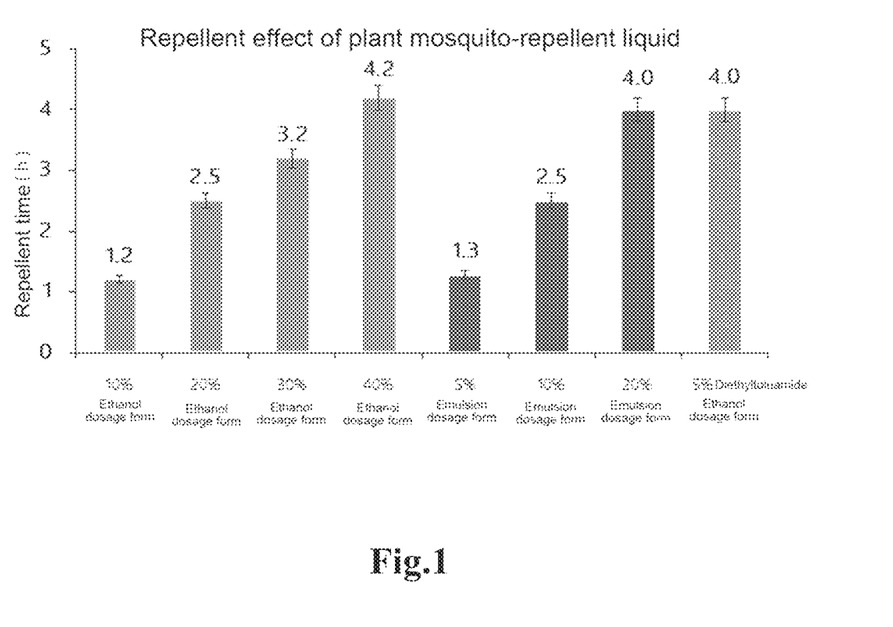
FIG. 1 shows the recommended proportion of the plant mosquito-repellent liquid of the present application.

Meanwhile, the inventor has measured the optimum used amount of the plant mosquito-repellent liquid through experiments (see FIG. 1).

2) Mosquito Repellent Effect—Human Evaluation

Human evaluation (repellent effect) tests were performed with plant composition extract (added in an amount of 20%, ethanol dosage form).

The test method is as follows:

Subject requirements: the age and sex are not limited, and a total of 73 subjects aged 2-60 years were selected, including 16 males and 57 females. The subjects were allowed to use a daily skin care product but not allowed to use any mosquito-repellent product other than the present product. The subjects were required to record and feedback the trial effect during the test.

Number of subjects: 73.

Test time: 1 week-2 weeks.

Evaluation content: the volunteers did self-evaluation prior to and after using the product to describe the repellent effect and the repellent time, and filled out a product use feedback form.

Figure 2:
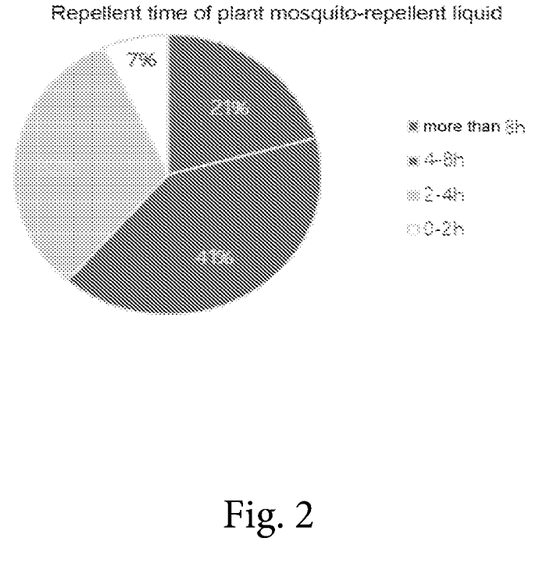
FIG. 2 shows the repellent time of the plant mosquito-repellent liquid of the present application for human body.
Figure 3:
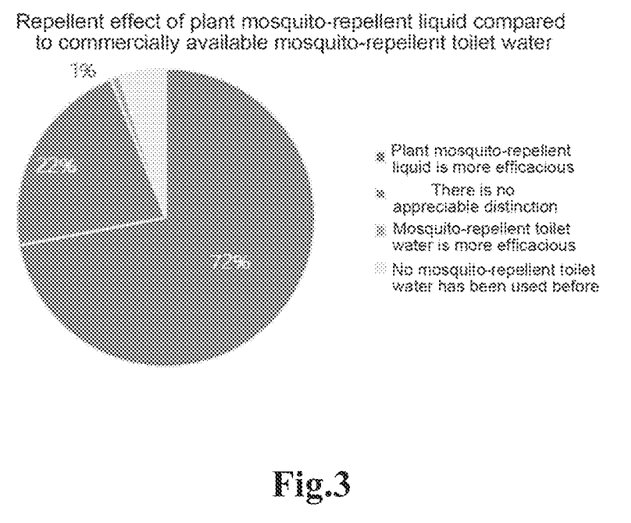
FIG. 3 shows the effect of the plant mosquito-repellent liquid of the present application compared with commercially available toilet water.

The statistical results are shown in FIGS. 2-3, and the clinical human evaluation results show that the extract has a remarkable repellent effect, has a general repellent time of 4-8 h and more than 8 h, and is more efficacious than the commercially available toilet water.

3) Bacteriostatic Effect

Products of Examples 1-5 and Comparison Examples 1-5 were sent to inhibition zone test.

The test method is as follows:

(1) Ordinary filter paper for laboratory use was punched into discs having a diameter of 0.5 cm with a puncher, and the discs were placed in a test tube for seal sterilization (at 121 degrees Celsius for 20 minutes).

(2) Cultured bacteria were made into a suspension with certain concentration; 1 ml of the bacterial suspension was introduced into a sterilized (at 121° C. for 20 minutes) culture dish; a proper amount (about 4 mm thick) of sterilized culture medium (with a temperature of about 45° C., such that you can touch the bottle wall without feeling hot) was poured thereto; the culture dish was slightly rotated to uniformly mix the culture medium and the bacteria suspension; and the mixture was allowed to stand to solidify into a flat plate.

(3) A piece of filter paper disc was clamped with sterile tweezers and placed into a test sample for soaking; when the filter paper disc was clamped out, it was held against the edge of the container a while to filter out redundant liquid; the filter paper disc was placed in the center of the solidified culture medium in the flat plate, and given a press by the tweezers with slight force to be fully attached to the culture medium.

(4) 2 replicates were run for each concentration as described above, and a filter paper disc soaked with sterile water was used as a blank control.

(5) After a certain period of time of culturing at proper temperature, observation was conducted, and the size of the inhibition zone was measured by using a ruler or a vernier caliper, and thereby the bacteriostatic ratio was calculated.

The test results are shown in table 2.

TABLE 2

| Sample No. | Inhibition zone diameter (cm) | | |
|---|---|---|---|
| | Escherichia coli | Staphylococcus aureus | Bacillus subtilis |
| Example 1 | 0.8 | 0.7 | 0.5 |
| Example 2 | 1.0 | 0.9 | 0.5 |
| Example 3 | 1.0 | 1.2 | 0.9 |
| Example 4 | 1.7 | 1.2 | 1.5 |
| Example 5 | 1.5 | 1.4 | 1.7 |
| Comparison Example 1 | 0.5 | 0.3 | 0 |
| Comparison Example 2 | 0.8 | 0.5 | 0.2 |
| Comparison Example 3 | 0.3 | 0.2 | 0.1 |
| Comparison Example 4 | 0.5 | 0.1 | 0 |
| Comparison Example 5 | 0.7 | 0.2 | 0.3 |

As can be seen in Table 2, the plant composition has remarkable effects of inhibiting *Escherichia coli*, *Staphylococcus aureus* and *Bacillus subtilis*, and particularly has remarkable effect of inhibiting *Bacillus subtilis*; while the bacteriostatic effect of the comparison examples were obviously inferior to that of the examples; moreover, Examples 4-5 have the best bacteriostatic effect.

4) Security Data

The plant composition and the extract preparation were subjected to a series of safety tests, and it has been proved from multiple angles that the plant composition and the extract preparation are safe and free of irritation and are suitable for a wide range of people.

1. Multiple (Acute) Skin Irritation Tests

Multiple (acute) skin irritation tests were performed with reference to "Safety and Technical Standards for Cosmetics (2015 Edition)", and the results demonstrate that: the plant composition extract is safe and non-irritating at 100% crude solution or at a lower concentration.

2. Acute Eye Irritation Test

Acute eye irritation test was performed with reference to "Safety and Technical Standards for Cosmetics (2015 Edition)", and the results demonstrate that: the plant composition extract is safe and non-irritating at a concentration of 20% or below.

3. Skin Allergy Test

Skin allergy test was performed with reference to "Safety and Technical Standards for Cosmetics (2015 Edition)", and the results demonstrate that: the plant composition extract has no sensitization at a concentration of 20% or below.

4. Phototoxicity Test

Skin allergy test was performed with reference to "Safety and Technical Standards for Cosmetics (2015 Edition)", and the results demonstrate that: the plant composition extract has no phototoxicity.

5. Human Skin Patch Test

Human skin patch test was performed with reference to "Safety and Technical Standards for Cosmetics (2015 Edition)", and the results demonstrate that: the plant composition extract has no adverse reaction to human body at a concentration of 20% or below.

Example 6

A skin care product was prepared by using the plant composition prepared by Example 5. Said skin care product comprises the following components in percentages by mass:

the adjuvant phase A: 3% of cetearyl alcohol/cetearyl glucoside, 3% of polydimethylsiloxane, 2% of stearic acid, 2% of isononyl isononanoate, 3% of jojoba oil, 2% of isopropyl myristate, 1% of Ve acetate, 5% of cetearyl alcohol, 2% of paraffin, 4% of hydrogenated polydecene and 3% of caprylic/capric triglyceride;

the adjuvant phase B: 0.1% of xanthan gum, 3% of glycerol, 4% of propylene glycol, 0.05% of disodium EDTA, 4% of α-mannan and 1% of PCA-Na;

the adjuvant phase C: 0.8% of acrylamide/ammonium acrylate copolymer/polyisobutylene/polysorbate-20;

the plant composition according to claim 1 or 2: 5%;

preservative: 0.1%;

with the balance being water.

A preparation method of the skin care product, comprising the following steps:

(1) butanediol, glycerol and xanthan gum of the adjuvant phase B were stirred uniformly for later use; the remaining raw materials of the adjuvant phase B were added into water and uniformly stirred, and the obtained mixture was added into the mixture of butanediol, glycerol and xanthan gum, heated to 83° C., and mixed uniformly;

(2) the materials of adjuvant phase A was heated to 83° C., and mixed uniformly;

(3) all the adjuvant phase A of the step (2) were added to adjuvant phase B of the step (1), homogenized at 2500 r/min for 6 min, then the adjuvant phase C was added thereto, homogenized at 2500 r/min for 2 min, and then stirred at a rotation rate of 40 r/min for 8 min; thereafter, the temperature was lowered at a cooling rate of 2° C./min by stirring at a stirring rate of 40 r/min;

(4) when the temperature was lowered to 48° C., the plant composition of Example 5 and preservative was added, stirred uniformly, and the temperature was continued to be lowered to 40° C. or less, thereby the skin care product was obtained.

Example 7

The skin care product comprises the following components in percentages by mass:

the adjuvant phase A: 2% of cetearyl alcohol/cetearyl glucoside, 4% of polydimethylsiloxane, 3% of stearic acid, 0.1% of isononyl isononanoate, 0.5% of jojoba oil, 1% of isopropyl myristate, 0.5% of Ve acetate, 3% of cetearyl alcohol, 1% of paraffin, 3% of hydrogenated polydecene and 1% of caprylic/capric triglyceride;

the adjuvant phase B: 0.2% of xanthan gum, 5% of glycerol, 5% of propylene glycol, 0.01% of disodium EDTA, 1% of α-mannan and 0.5% of PCA-Na;

the adjuvant phase C: 1% of acrylamide/ammonium acrylate copolymer/polyisobutylene/polysorbate-20;

the plant composition according to claim 1 or 2: 10%;

preservative: 0.2%;

with the balance being water.

The preparation method is the same as that of Example 6.

Example 8

The skin care product comprises the following components in percentages by mass:

the adjuvant phase A: 1.5% of cetearyl alcohol/cetearyl glucoside, 1% of polydimethylsiloxane, 0.1% of stearic acid, 3% of isononyl isononanoate, 6% of jojoba oil, 5% of isopropyl myristate, 1.5% of Ve acetate, 0.5% of cetearyl alcohol, 3% of paraffin, 5% of hydrogenated polydecene and 5% of caprylic/capric triglyceride;

the adjuvant phase B: 0.05% of xanthan gum, 5% of glycerol, 3% of propylene glycol, 0.1% of disodium EDTA, 5% of α-mannan and 2% of PCA-Na;

the adjuvant phase C: 0.2% of acrylamide/ammonium acrylate copolymer/polyisobutylene/polysorbate-20;

the plant composition according to claim 1 or 2: 20%;

preservative: 0.05%;

with the balance being water.

The preparation method is the same as that of Example 6.

The products of Example 5 and Examples 6-8 were subjected to a mosquito repellent effect test, the test method was as described above, and the results are shown in FIG. 1. The plant composition showed a superior repellent effect, and the repellent time had a dose dependence; and the mosquito repellent time of Example 8 (the plant composition was added in an amount of 20%, emulsion dosage form) and Example 5 (40% of test concentration, ethanol dosage form) reaches 4.00 h and 4.20 h respectively, meeting the national repellent B-level standard. The emulsion preparation can achieve remarkable mosquito repellent effect by adding the extract at a relatively low concentration, because some substances in the emulsion play a slow releasing effect.

As can be seen from the above examples, in the present application, by means of reasonably formulating appropriate lemon eucalyptus, lavender and mint and adjusting the contents thereof, synergistic effect among said three components is expressed, ensuring a repellent effect while repellent time is prolonged, and introducing the plant composition into skin care products enhances a repellent effect while being safe and non-irritating.

The applicant declares that the present application illustrates the detailed technological equipment and process of the present application by the above examples, but the present application is not limited to the above detailed technological equipment and process, that is, it does not mean that the present application must rely on the above detailed technological equipment and process in order to be implemented. It will be apparent to those skilled in the art that any modifications to the present application, any equivalent replacement of each raw material of the products of the present invention and the addition of auxiliary ingredients, the selection of specific embodiment and the like all fall into the protection scope and the disclosure scope of the present invention.

What is claimed is:

1. A plant composition, comprising the following components in parts by weight: 20-60 parts of lemon eucalyptus, 3-20 parts of lavender, and 2-15 parts of mint,
   wherein the plant composition is prepared by a method comprising the following steps:
   (1) raw materials are pretreated, which comprises pretreatment of lemon eucalyptus, pretreatment of lavender and pretreatment of mint;
   (2) the treated raw materials are blended according to the formula amounts, then subjected to ultrasonic treatment with pure water, and then extracted by distillation;
   (3) the distillate obtained from the extraction in the step (2) is allowed to stand for layering, and an essential oil in the upper layer is collected and blended with dipropylene glycol to obtain the plant composition;
   wherein the pretreatment of lemon eucalyptus comprises the following specific steps: lemon eucalyptus leaves are collected, cleaned, sprinkled with a 30-70% ethanol aqueous solution, and thus soaked in the 30-70% ethanol aqueous solution, flipped once every 5-12 h, and sealed for 1-3 days, and then the soaked lemon eucalyptus leaves are air dried;
   the pretreatment of lavender comprises the following specific steps: lavender flower branches are collected, cleaned, soaked in a 0.5-10% sodium chloride solution for 7-12 h, and then the soaked lavender is air dried; and
   the pretreatment of mint comprises the following specific steps: mint leaves are collected, cleaned, air dried, and then dried at 30-50° C. for 1-5 h.

2. The plant composition according to claim 1, wherein the plant composition comprises the following components in parts by weight: 30-50 parts of lemon eucalyptus, 5-15 parts of lavender, and 3-12 parts of mint.

3. The plant composition according to claim 2, wherein the plant composition comprises the following components in parts by weight: 33-48 parts of lemon eucalyptus, 5-10 parts of lavender, and 4-8 parts of mint.

4. A plant mosquito-repellent liquid comprising an effective amount of the plant composition according to claim 1.

5. A skin care product, comprising an effective amount of the plant composition according to claim 1.

6. The skin care product according to claim 5, wherein the plant composition accounts for 5-50% by mass of the skin care product.

7. The skin care product according to claim 6, wherein the plant composition accounts for 10-40% by mass of the skin care product.

8. The skin care product according to claim 5, wherein the skin care product further comprises an adjuvant;
   the adjuvant is an adjuvant phase A, an adjuvant phase B, an adjuvant phase C and a preservative;
   the adjuvant phase A is a mixture of cetearyl alcohol/cetearyl glucoside, polydimethylsiloxane, stearic acid, isononyl isononanoate, jojoba oil, isopropyl myristate, Ve acetate, paraffin, hydrogenated polydecene or caprylic/capric triglyceride;
   the adjuvant phase B is a mixture of xanthan gum, glycerol, propylene glycol, disodium EDTA, α-mannan or PCA-Na;
   the adjuvant phase C is acrylamide/ammonium acrylate copolymer/polyisobutylene/polysorbate-20.

9. The skin care product according to claim 8, wherein the adjuvant phase A comprises the following components in percentages by mass: 1.5-3% of cetearyl alcohol/cetearyl glucoside, 1-4% of polydimethylsiloxane, 0.1-3% of stearic acid, 0.1-3% of isononyl isononanoate, 0.5-6% of jojoba oil, 1-5% of isopropyl myristate, 0.5-1.5% of Ve acetate, 1-3% of paraffin, 3-5% of hydrogenated polydecene and 1-5% of caprylic/capric triglyceride;
   the adjuvant phase B comprises the following components in percentages by mass: 0.05-0.2% of xanthan gum, 2-5% of glycerol, 3-5% of propylene glycol, 0.01-0.1% of disodium EDTA, 1-5% of α-mannan and 0.5-2% of PCA-Na;
   the adjuvant phase C accounts for 0.2-1% by mass of the skin care product;
   the preservative accounts for 0.05-0.2% by mass of the skin care product.

10. The skin care product according to claim 9, wherein the skin care product comprises skin care product in percentages by mass:
   the adjuvant phase A: 1.5-3% of cetearyl alcohol/cetearyl glucoside, 1-4% of polydimethylsiloxane, 0.1-3% of stearic acid, 0.1-3% of isononyl isononanoate, 0.5-6% of jojoba oil, 1-5% of isopropyl myristate, 0.5-1.5% of Ve acetate, 1-3% of paraffin, 3-5% of hydrogenated polydecene and 1-5% of caprylic/capric triglyceride;

the adjuvant phase B: 0.05-0.2% of xanthan gum, 2-5% of glycerol, 3-5% of propylene glycol, 0.01-0.1% of disodium EDTA, 1-5% of α-mannan and 0.5-2% of PCA-Na;

the adjuvant phase C: 0.2-1% of acrylamide/ammonium acrylate copolymer/polyisobutylene/polysorbate-20;

the plant composition according to claim 1: 10-40%;

preservative: 0.05-0.2%;

with the balance being water.

\* \* \* \* \*

UNITED STATES PATENT AND TRADEMARK OFFICE
CERTIFICATE OF CORRECTION

PATENT NO. : 11,033,486 B2
APPLICATION NO. : 16/480435
DATED : June 15, 2021
INVENTOR(S) : Yinmao Dong et al.

It is certified that error appears in the above-identified patent and that said Letters Patent is hereby corrected as shown below:

On the Title Page

Item (30) Foreign Application Priority Data: "January 24, 2017 (CN)...201710052705.X" is corrected to read --201710052709.X--

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*